US009427139B2

United States Patent
Tinkham et al.

(10) Patent No.: US 9,427,139 B2
(45) Date of Patent: Aug. 30, 2016

(54) POSITIONING SYSTEM FOR MANIPULATING A TREATMENT INSTRUMENT AT THE END OF A MEDICAL DEVICE

(75) Inventors: Brian Tinkham, South Boston, MA (US); Kevin Richardson, Austin, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2660 days.

(21) Appl. No.: 11/779,532

(22) Filed: Jul. 18, 2007

(65) Prior Publication Data

US 2008/0021269 A1     Jan. 24, 2008

Related U.S. Application Data

(60) Provisional application No. 60/832,594, filed on Jul. 24, 2006.

(51) Int. Cl.
*A61B 1/00*     (2006.01)
*A61B 1/04*     (2006.01)
*A61B 1/018*     (2006.01)
*A61B 1/005*     (2006.01)

(52) U.S. Cl.
CPC ............ *A61B 1/018* (2013.01); *A61B 1/00098* (2013.01); *A61B 1/0052* (2013.01)

(58) Field of Classification Search
USPC ......... 600/104, 106, 107, 114, 115, 127–130, 600/139–152, 433–435; 604/103.04; 606/205–209
See application file for complete search history.

(56) References Cited

U.S. PATENT DOCUMENTS

| | | | |
|---|---|---|---|
| 5,460,168 A | 10/1995 | Masubuchi et al. | |
| 5,924,976 A * | 7/1999 | Stelzer | A61B 1/00098 600/106 |
| 6,027,460 A * | 2/2000 | Shturman | A61M 25/0133 600/129 |
| 6,099,464 A | 8/2000 | Shimizu et al. | |
| 6,824,509 B2 * | 11/2004 | Yamaya et al. | 600/106 |
| 7,063,659 B2 | 6/2006 | Goto et al. | |
| 7,699,836 B2 * | 4/2010 | Sugita et al. | 606/1 |
| 2003/0040657 A1 | 2/2003 | Yamaya et al. | |

(Continued)

FOREIGN PATENT DOCUMENTS

| | | | | |
|---|---|---|---|---|
| JP | 56-156144 | | 2/1981 | |
| JP | 56156144 A | * | 12/1981 | A61B 1/00 |

(Continued)

OTHER PUBLICATIONS

International Search Report dated Nov. 28, 2007, for corresponding International Application No. PCT/US2007/073769 (five pages).

*Primary Examiner* — Ryan Henderson
(74) *Attorney, Agent, or Firm* — Bookoff McAndrews, PLLC

(57) ABSTRACT

Embodiments of the invention include a medical device for accessing a patient's body portion and used for diagnosis and treatment of medical conditions. Embodiments of the invention may include a particular endoscopic positioning mechanism for placing an endoscope and an additional treatment device within desired body portions in order to assist in diagnosis and treatment of anatomical diseases and disorders. In particular, a medical device according to an embodiment of the invention includes a positioning mechanism configured for movement through at least two degrees of freedom.

31 Claims, 9 Drawing Sheets

(56) References Cited

U.S. PATENT DOCUMENTS

2005/0049455 A1* 3/2005 Ootawara et al. ............ 600/107
2005/0096501 A1* 5/2005 Stelzer et al. ................ 600/101
2008/0287961 A1* 11/2008 Miyamoto ......... A61B 1/00098
606/127

FOREIGN PATENT DOCUMENTS

JP    2003-310545 A    11/2003
WO    WO 2007/097797 A2    8/2007

* cited by examiner

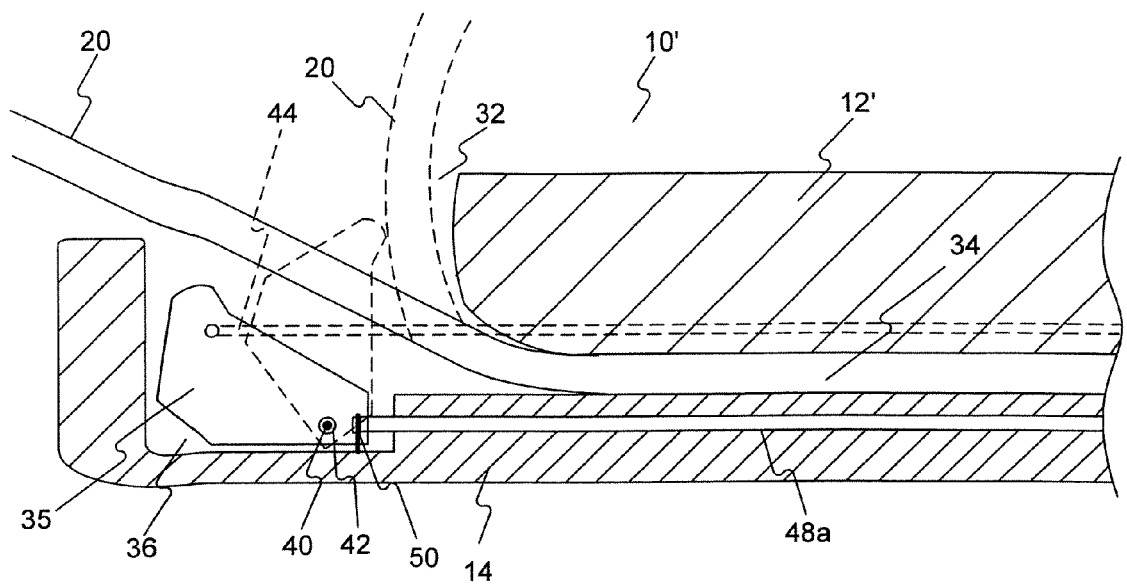
FIG. 4
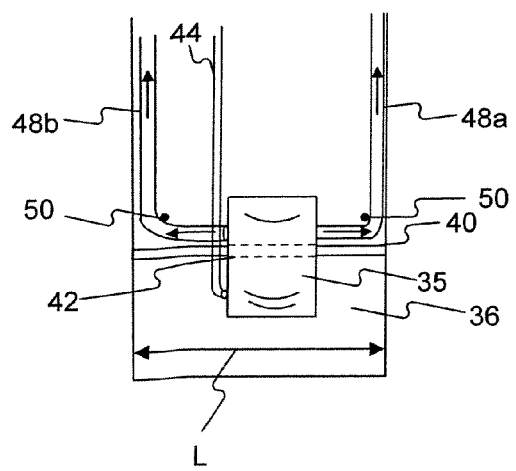
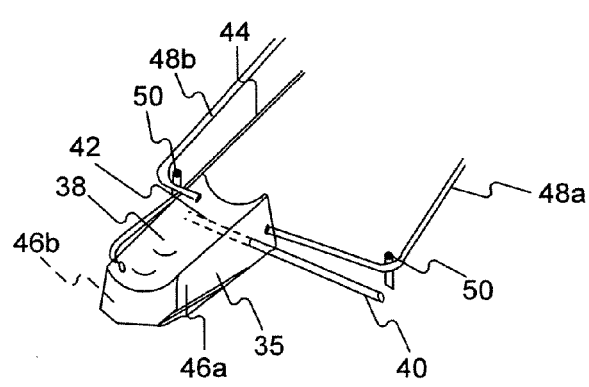
FIG. 5  FIG. 6A

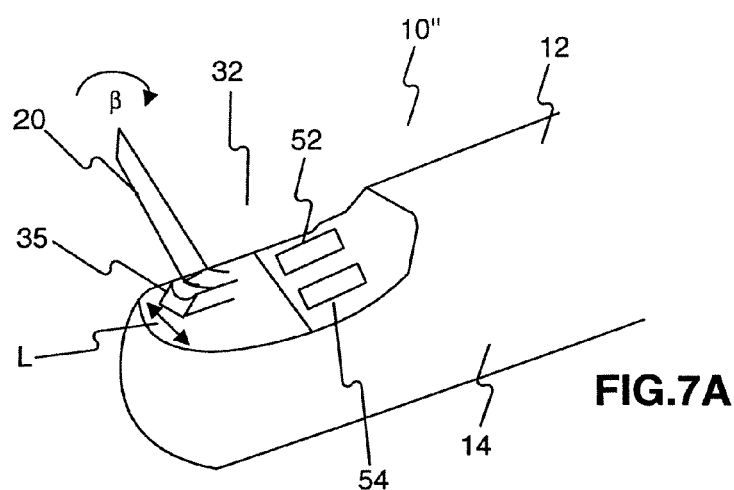
FIG.7A
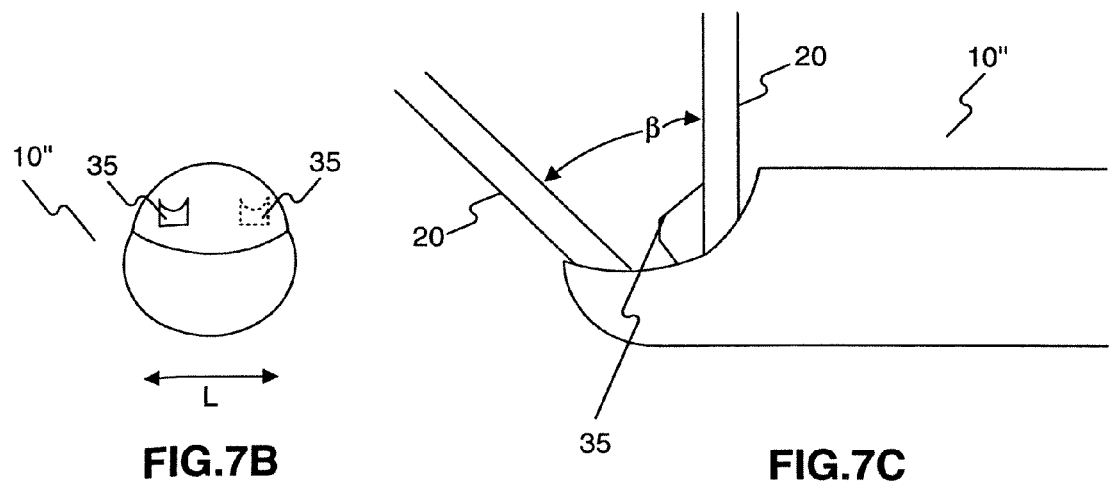
FIG.7B
FIG.7C

POSITIONING SYSTEM FOR MANIPULATING A TREATMENT INSTRUMENT AT THE END OF A MEDICAL DEVICE

CROSS-REFERENCE TO RELATED APPLICATIONS

This application claims the benefit of U.S. Provisional Application No. 60/832,594, filed Jul. 24, 2006, under 35 U.S.C. §119(e). The entire content of that provisional application is expressly incorporated by reference herein.

FIELD OF THE INVENTION

The invention relates to an endoscope system for accessing a patient's body portion and used for diagnosis and treatment of medical conditions. For example, embodiments of the invention may include a particular endoscopic positioning mechanism for placing an endoscope and an additional treatment device within desired body portions in order to assist in diagnosis and treatment of anatomical diseases and disorders.

BACKGROUND OF THE INVENTION

Endoscopes for medical use have been adopted for various diagnostic and medical treatment procedures. Endoscopes have been used for the diagnosis and treatment of a wide range of diseases and disorders that often require a physician to access the tortuous and relatively small cross-sectional areas of a patient's internal anatomical body lumens. A patient's pancreaticobiliary system (including the anatomical regions of the gall bladder, pancreas, and the biliary tree), for example, is accessed for diagnosis, and/or treatment of disorders of certain portions of the digestive system.

During treatment of the digestive system, endoscopes are often used to access and visualize a patient's pancreaticobiliary system. Once the endoscope is positioned in the desired body portion, a treatment instrument can be advanced through the working channel of the endoscope to the desired body portion. The endoscope and treatment instrument may then be manipulated as desired for visualization and treatment respectively.

Endoscopic retrograde cholangiopancreatography (ERCP) is one example of a medical procedure that uses an endoscope. ERCP enables the physician to diagnose problems in the liver, gallbladder, bile ducts, and pancreas. The liver is a large organ that, among other things, makes bile that helps with digestion. The gallbladder is a small, pear-shaped organ that stores bile until it is needed for digestion. The bile ducts are tubes that carry bile from the liver to the gallbladder and small intestine. These ducts are sometimes called the biliary tree. The pancreas is a large gland that produces chemicals that help with digestion and hormones such as insulin.

The biliary system delivers bile produced by the liver to the duodenum where the bile assists other gastric fluids in digesting food. The biliary system includes the liver, as well as a plurality of bodily channels and organs that are disposed between the liver and the duodenum. Within the liver lobules, there are many fine "bile canals" that receive secretions from the hepatic cells. The canals of neighboring lobules unite to form larger ducts, and these converge to become the "hepatic ducts." They merge, in turn, to form the "common hepatic duct." The "common bile duct" is formed by the union of the common hepatic and the cystic ducts. It leads to the duodenum, where its exit is guarded by a sphincter muscle. This sphincter normally remains contracted until the bile is needed, so that bile collects in the common bile duct and backs up to the cystic duct. When this happens, the bile flows into the gallbladder and is stored there.

ERCP is used primarily to diagnose and treat conditions of the bile ducts, including gallstones, inflammatory strictures (scars), leaks (from trauma and surgery), and cancer. ERCP combines the use of x-rays and an endoscope. Through the endoscope, the physician can see the inside of the stomach and duodenum, and inject dyes into the ducts in the biliary tree and pancreas so they can be seen on x-rays.

An ERCP is performed primarily to identify a problem in the bile ducts or pancreas. Other applications are directed more towards therapy rather than only diagnosis. For example, other procedures include using endoscopes for stone removal and sphincterotome. In addition, combined diagnostic and therapeutic procedures may be performed. For example, if a gallstone is found during the exam, it can often be removed by means of a treatment instrument, eliminating the need for major surgery. If a blockage in the bile duct causes yellow jaundice or pain, it can be relieved through the use of a treatment instrument inserted through the endoscope.

Since endoscopes are often used to access the tortuous and relatively small cross-sectional areas of a patient's internal anatomical body lumens, repeated manipulation and positioning of an endoscope during a medical procedure can cause problematic side-effects. For example, repeated manipulation and positioning of the endoscope can cause unnecessary trauma to a patient's internal tissues. Improper placement and repeated attempts to access a desired treatment region can exacerbate tissue trauma as well as unnecessarily prolong the medical procedure. Accordingly, there is a need for more precise endoscope manipulation as well as manipulating an underlying treatment instrument through an access channel of an endoscope.

Thus, it is desirable to have an endoscope assembly that can more precisely access the tortuous and relatively small cross-sectional areas of certain anatomical body lumens, and more precisely manipulate a treatment device provided within an access channel of an endoscope.

SUMMARY OF THE INVENTION

Embodiments of the present invention are directed to an improved endoscope system and a positioning device for manipulating a treatment device that obviates one or more of the limitations and disadvantages of prior medical devices.

In one embodiment, a medical device comprises an elongated flexible tube including a distal end and a proximal end and defining a lumen extending from the proximal end to an aperture at the distal end. A positioning mechanism is positioned at the distal end of the flexible tube proximate the aperture. The positioning mechanism is configured for movement through at least two degrees of freedom to transmit force to a treatment instrument extending through the lumen and to control a direction at which a treatment instrument extends from the aperture.

In various embodiments, the device may include one or more of the following additional features: wherein the positioning mechanism is housed within a recess at the distal end of the flexible tube, the positioning mechanism being configured for rotation about a pin within the recess; wherein the positioning mechanism is configured for lateral displacement within the recess and along the pin; wherein the positioning mechanism is configured for longitudinal displacement within the recess; wherein the positioning mechanism includes an elongated slot extending therethrough that receives the pin such that the positioning mechanism is configured for longitudinal movement relative to the pin; wherein a resilient sponge material is included within a portion of the elongated slot such that the positioning mechanism returns to a resting longitudinal position when longitudinally directed actuation forces are no longer applied to the positioning mechanism; wherein the positioning mechanism is configured for angular displacement through combined lateral and longitudinal displacement of the positioning mechanism; wherein the pin comprises a resilient, flexible material such that the positioning mechanism is configured for further angular displacement through combined lateral and longitudinal displacement of the positioning mechanism; further comprising a spring connected at one end to a second side of the positioning mechanism, opposite the first side of the positioning mechanism, and connected at another end to the flexible tube such that after actuation of the pull wire the positioning mechanism returns to a resting position; wherein the positioning mechanism comprises a movable positioning sleeve having a roller positioned on the distal end thereof, the roller being rotatable relative to the sleeve and including a lumen therethrough configured for receiving a treatment instrument extended distally beyond the lumen; wherein the positioning mechanism is configured for lateral displacement in a first direction through actuation of a pull wire connected to a first side of the positioning mechanism; wherein the positioning mechanism is configured for lateral displacement in a second direction, opposite the first direction, through actuation of a pull wire connected to a second side of the positioning mechanism, opposite the first side of the positioning mechanism; wherein the pull wires connected to the first and second sides of the positioning mechanism extend laterally away from the positioning mechanism then wrap around and extend proximally away from force transmission posts located within the recess; wherein the positioning mechanism includes a concave surface configured to maintain contact with a treatment instrument extended distally beyond the lumen; wherein the aperture is a side facing aperture opening laterally along the flexible tube; wherein the positioning mechanism is configured for movement through at least three degrees of freedom; wherein the positioning mechanism is rotatable about three orthogonal axes; wherein the positioning mechanism comprises a roller rotatable relative to the aperture, the roller including a lumen therethrough configured for receiving a treatment instrument extended distally beyond the lumen; wherein a proximal end of the lumen through the roller is configured to maintain alignment with the lumen of the elongated flexible tube; wherein the lumen through the roller exhibits a cone shape having a distal opening more narrow than a proximal opening; further comprising a sleeve extending within the lumen of the roller and movable within and distally beyond the lumen of the roller; wherein the sleeve is configured for receiving a treatment instrument and imparting rotation to the treatment instrument upon rotation of the sleeve; wherein the roller is configured for rotation about three orthogonal axes; wherein rotation of the roller relative to the aperture is achieved through the actuation of pull wires, each fixedly attached to a predetermined location along the roller; further comprising a wedge having an inclined surface positioned distally of the roller and wherein the rotation of the roller relative to the aperture is achieved through proximal movement of the base beneath the roller; wherein attachment of each pull wire to the roller occurs at a constant predetermined distance from a distal point of exit of the lumen of the roller; wherein at least three pull wires are fixedly attached to the roller; wherein the medical device is an endoscope that includes visualization components therein; wherein the medical device is an endoscope that includes illumination components therein; wherein the medical device is an endoscope that includes an additional positioning mechanism for achieving controlled deflection of the elongated flexible tube.

In another embodiment, a medical device comprises an elongated flexible tube including a distal end and a proximal end and defining a lumen extending from the proximal end to an aperture at the distal end. A deflection mechanism is housed within the distal end of the flexible tube opposite the aperture, the deflection mechanism being configured for rotation about a pin extending within the recess and for lateral displacement along the pin.

In various embodiments, the device may include one or more of the following additional features: wherein the deflection mechanism is configured for longitudinal displacement within the recess; wherein the deflection mechanism includes an elongated slot extending therethrough that receives the pin such that the deflection mechanism is configured for longitudinal movement relative to the pin; wherein a resilient sponge material is included within a portion of the elongated slot such that the deflection mechanism returns to a resting longitudinal position when longitudinally directed actuation forces are no longer applied to the deflection mechanism; wherein the deflection mechanism is configured for angular displacement through combined lateral and longitudinal displacement of the deflection mechanism; wherein the pin comprises a resilient, flexible material such that the deflection mechanism is configured for further angular displacement through combined lateral and longitudinal displacement of the deflection mechanism; wherein the deflection mechanism includes a concave surface configured to maintain contact with a treatment instrument extended distally beyond the lumen; wherein the aperture is a side facing aperture opening laterally along the flexible tube; wherein the deflection mechanism is configured for lateral displacement in a first direction through actuation of a pull wire connected to a first side of the deflection mechanism; wherein the deflection mechanism is configured for lateral displacement in a second direction, opposite the first direction, through actuation of a pull wire connected to a second side of the deflection mechanism, opposite the first side of the deflection mechanism; and wherein the pull wires connected to the first and second sides of the deflection mechanism extend laterally away from the deflection mechanism then wrap around and extend proximally away from force transmission posts located within the recess.

In another embodiment, a medical device comprises an elongated flexible tube including a distal end and a proximal end and defining a lumen extending from the proximal end to an aperture at the distal end. A roller is positioned at the distal end of the flexible tube and rotatable relative to the aperture, the roller including a lumen therethrough configured for receiving a treatment instrument extended distally beyond the lumen.

In various embodiments, the device may include one or more of the following additional features: further comprising a movable sleeve and wherein the roller is positioned on the distal end thereof, the roller being rotatable relative to the sleeve; a sleeve extending within the lumen of the roller and movable within and distally beyond the lumen in the roller; wherein the sleeve is configured for receiving a treatment instrument and imparting rotation to the treatment instrument upon rotation of the sleeve; wherein the roller is configured for rotation about three orthogonal axes; wherein rotation of the roller relative to the aperture is achieved through the actuation of pull wires, each fixedly attached to a predetermined location along the roller; further comprising a wedge having an inclined surface positioned distally of the roller and wherein the rotation of the roller relative to the aperture is achieved through proximal movement of the inclined wedge surface beneath the roller; further comprising a movable base positioned distally of the roller and wherein the rotation of the roller relative to the aperture is achieved through longitudinal and lateral movement of the base beneath the roller; wherein attachment of each pull wire to the roller occurs at a constant predetermined distance from a distal point of exit of the lumen of the roller; wherein at least three pull wires are fixedly attached to the roller; wherein the medical device is an endoscope that includes visualization components therein; wherein the medical device is an endoscope that includes illumination components therein; wherein the medical device is an endoscope that includes an additional positioning mechanism for achieving controlled deflection of the elongated flexible tube.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 4 is cross-sectional view of a distal portion of an endoscope according to an embodiment of the present invention.

FIG. 5 is a top view of components of an instrument positioning device according to an embodiment of the present invention.

FIG. 6A is a perspective view of components of an instrument positioning device according to an embodiment of the present invention.

FIG. 7A is a perspective view of a distal part of an endoscope according to an embodiment of the present invention.

FIG. 7B is a front view of a distal part of an endoscope according to an embodiment of the present invention.

FIG. 7C is a side view of a distal part of an endoscope according to an embodiment of the present invention.

DESCRIPTION OF THE EMBODIMENTS

Figure 1:
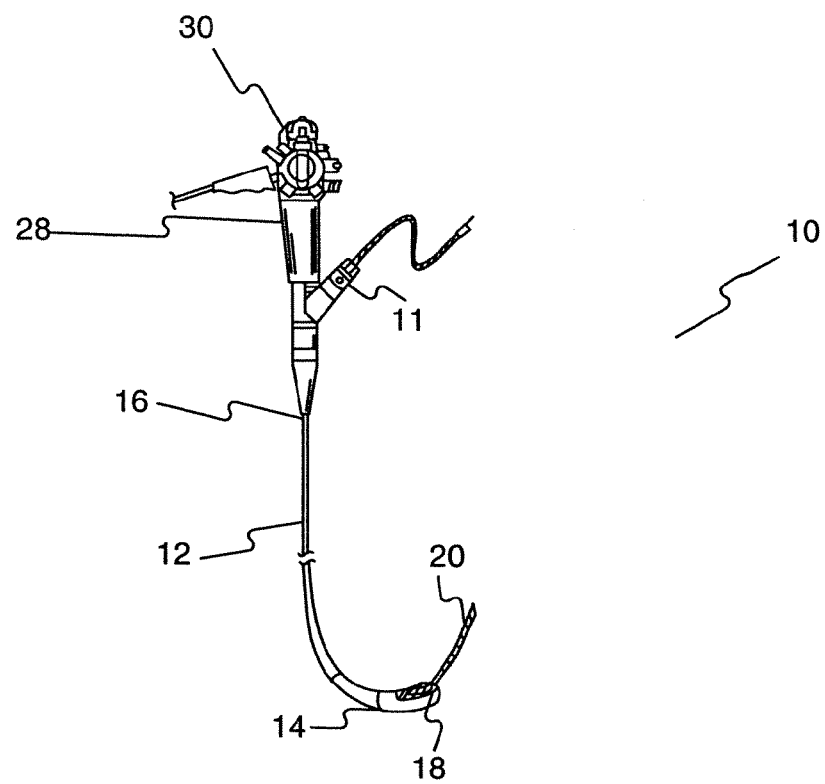
FIG. 1 is a perspective view of a prior art endoscope system.

Reference will now be made in detail to the exemplary embodiments of the invention, examples of which are illustrated in the accompanying drawings. Wherever possible, the same reference numbers will be used throughout the drawings to refer to the same or like parts. The drawing figures of this application are intended to provide a general understanding of the working elements of the underlying system. Accordingly, unless explicitly stated, the figures do not represent a literal depiction of proportional dimensions or the precise locations for the illustrated inter-related components.

According to exemplary embodiments, the invention relates to a medical device for positioning a treatment device and/or viewing a patient's internal body portion. In embodiments that use a treatment device in an endoscopic medical procedure, the treatment device can be advanced through a working channel of an endoscope, including an endoscope specifically designed and/or sized for use with the treatment device, and into a tissue tract. For purposes of this disclosure, "treatment device" or "treatment instrument" includes, for example, any working medical device advanced through a working channel of an endoscope and for use during an endoscopic procedure. Exemplary treatment instruments include, but are not limited to, guide wires, cutting or grasping forceps, biopsy devices, snare loops, injection needles, cutting blades, scissors, retractable baskets, retrieval devices, ablation and/or electrophysiology catheters, stent placement devices, surgical stapling devices, and balloon catheters.

FIG. 1 illustrates a known endoscope system. For purposes of this disclosure, "distal" refers to the end further from the device operator during use and "proximal" refers to the end closer to the device operator during use. FIG. 1 depicts an endoscope 10 including a flexible outer tube 12 extending between a distal end 14 and a proximal end 16 of the device. Endoscope 10 includes a treatment device insertion port 11 for receiving a treatment device 20 into a working channel of the endoscope 10. The distal end 14 of the endoscope system 10 includes a side facing operation window 18 that can include visualization and lighting components for viewing during a treatment procedure. In addition, a working channel (not shown) extends within the endoscope 10 and terminates at the operation window 18, thereby allowing the treatment instrument 20 to be extended from the distal end of the endoscope 10. The extension of the treatment instrument 20 at a desired treatment site can be then be viewed through the visualization components, which transmit images to the proximal end of the endoscope 10, as in known in the art. While FIG. 1 illustrates a side facing operation window 18, both front/forward facing and oblique/intermediate angled windows are known.

Figure 2:
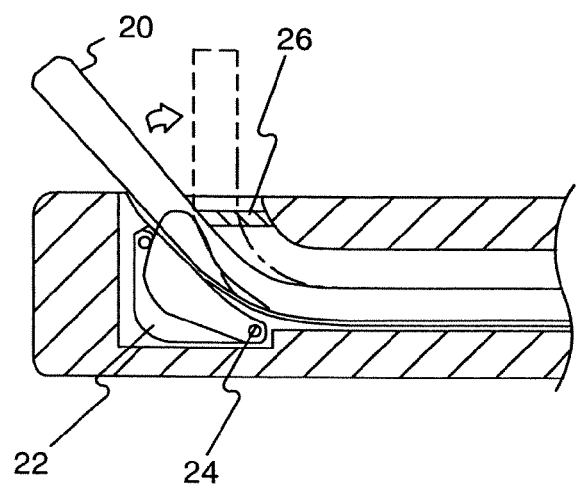
FIG. 2 is a cross-sectional view illustrating the structure of a known elevator device.

FIG. 2 illustrates a cross-sectional view of a distal portion of a known endoscope system including a deflecting lever/elevator device for deflecting a treatment instrument as the instrument is extended beyond a working channel of an endoscope. As seen in FIG. 2, a deflecting lever 22 is rotated clockwise about a pin 24 by means of a pull wire 26 connected to an upper portion of the deflecting lever 22. Upon actuation of the pull wire 26 through proximal movement thereof, the deflecting lever 22 deflects the treatment device 20 in order to alter the angle at which the treatment device 20 exits the endoscope's working channel, resulting in the position of device 20 shown by the dashed lines in FIG. 2. By means of pull wire 26, the endoscope operator can control the placement of the treatment instrument 20 as it is positioned during a medical procedure.

As seen in FIG. 1, a handle 28 at the proximal end 16 of the device can include various positioning controls 30 to effectuate bending and rotation of the flexible outer tube 12 for positioning of the device during a medical procedure. In addition, the handle can include a distinct positioning control for actuation of the deflection lever pull wire 26. During a medical procedure such as, for example, an ERCP procedure, the treatment instrument 20 must be precisely inserted into a particular duct in the biliary tree. While the use of a deflection lever 26 is capable of altering the angle at which the treatment device exits the endoscope, precise positioning often requires repeated manipulation of the distal end of the endoscope including the operation window in order to achieve proper placement of the treatment device 20. As noted above, this repeated manipulation of the underlying endoscope 10 can lead to tissue trauma and unnecessarily prolong the entire medical procedure.

As seen in the embodiment of FIG. 2, the deflection lever 26 is displaceable about a single axis (i.e. the axis coincident with the pin 24). Accordingly, lever 26 is movable about and only effectuates movement of the treatment device 20 through one degree of freedom. Precise manipulation of a treatment instrument is increased when manipulation is afforded along or about an additional particular coordinate axis. A degree of freedom describes flexibility of motion added due to displacement along or about a particular coordinate axis.

Figure 3:
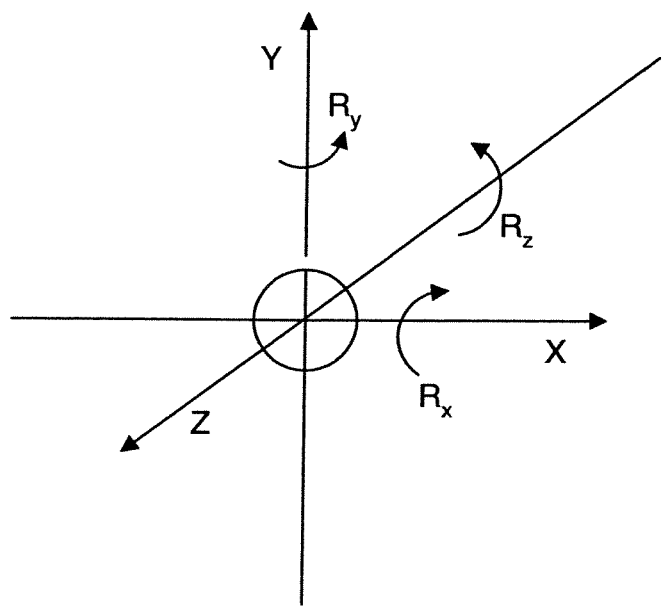
FIG. 3 illustrates an exemplary coordinate system for designating translational and rotational displacement of elements in a system of connected bodies.

FIG. 3 illustrates a known Cartesian coordinate system illustrating the three orthogonal axes of X, Y, and Z. A linkage or any system of connected bodies that has complete freedom of motion (even if only in a limited area) has six degrees of freedom. Three modes are translation (i.e. the ability to move in each of three dimensions in a direction parallel to each of the three orthogonal axes). An additional three modes are rotation, i.e. the ability to change an angular position around the three orthogonal axes. Only three degrees of freedom are necessary to move a structure anywhere in space, but additional degrees of freedom provide more versatility. For example, each of the following is one degree of freedom: moving up and down along the Y axis (heaving); moving left and right along the X axis (swaying); moving forward and back along the Z axis (surging); tilting up and down (rotation Rx about the X axis); turning left and right (rotation Ry about the Y axis); and tilting side to side (rotation Rz about the Z axis). Accordingly, a positioning mechanism that effectuates movement through more than one degree of freedom will allow for more precise positioning of an underlying treatment device.

FIG. 4 illustrates a cross-sectional view of a distal portion of an endoscope according to an embodiment of the present invention. FIG. 4 depicts a cross-sectional view of a distal end 14 of an improved endoscope 10'. The distal portion of endoscope 10' includes an exterior flexible outer tube 12', a side facing operation window aperture 32, and a working channel 34 forming a lumen within the endoscope 10' and extending from the proximal end of the endoscope 10' and terminating at the operation window aperture 32. A deflection elevator in the form of a positioning block 35 is housed within a recess 36 at the distal end of the endoscope 10' at a position opposite the operation window aperture 32.

Figure 6B:
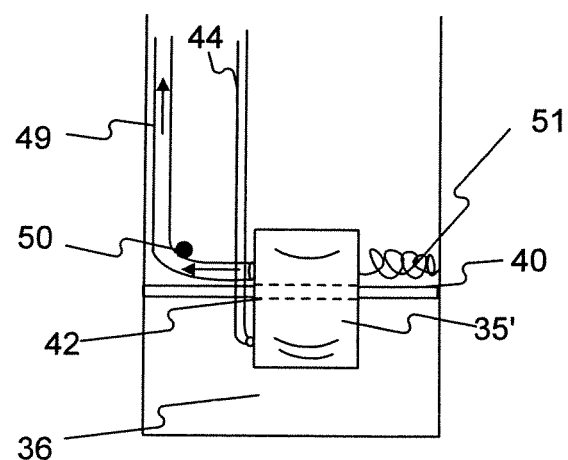
FIG. 6B is a top view of components of an alternative instrument positioning device according to an embodiment of the present invention.

FIGS. 5-6B illustrate top and perspective views, respectively, of exemplary displacement mechanisms which control movement of the positioning block 35. As seen in FIG. 6A, positioning block 35 includes a curved concave surface 38 configured to maintain contact with a treatment instrument extended beyond the endoscope's working channel (see FIG. 4). The curved surface 38 of the positioning block 35 acts as the surface for transferring a deflection force against a treatment instrument 20 during extension of the treatment instrument 20. Alternatively, the positioning block 35 may include a closed top surface thereby forming an internal lumen for receiving a treatment instrument therein. As another alternative the positioning block can be provided with a notch or channel formed in the concave surface 38. The notch can be provided with a "v" shaped trough sized to releasable engage a treatment instrument therein in a passive friction fit engagement.

The positioning block 35 is disposed for operative connection within the distal end of the endoscope through a pin 40, which extends laterally within the endoscope's distal end 14 and perpendicular to the longitudinal axis of outer tube 12'. The pin 40 extends laterally within a pin aperture 42 formed in the body of positioning block 35. The pin 40 is fixed to the flexible tube 12' such that the positioning block 35 is configured to rotate about and translate laterally relative to the pin 40. Pin 40 extends through the aperture 42 but is not fixedly attached to positioning block 35. Accordingly, the positioning block 35 is configured to deflect a treatment instrument, such as, for example, device 20 extending within working channel 34. Positioning block 35 is configured for clockwise rotation about rotation pin 40 through actuation of a pull wire 44, illustrated in dashed lines in FIG. 4. Pull wire 44 is connected at an upward offset distal position along the positioning block 35 such that proximal movement of pull wire 44 rotates the positioning block 35 about rotation pin 40. As seen in dashed lines in FIG. 4, the pull wire 44 extends proximally within a pull wire channel (not shown) of the endoscope where it extends for connection with a positioning control device at a handle at the endoscope's proximal end. As pull wire 44 is displaced in a proximal direction, the positioning block 35, and in turn, the treatment instrument 20 (as seen in dashed lines in FIG. 4) are rotated such that the angle at which treatment instrument 20 extends from the endoscope 10' is increased.

Pull wire 44, for example, can extend for connection to a bending lever or rotation wheel control device where proximal actuation can be effected by an operator. While a pull wire element is illustrated as the mechanism for deflection of the positioning block 35, alternative deflection mechanisms can be used, including, but not limited to, forward acting push wires, or stylets, electronic piezoelectric bending transducers, and an inflatable cuff element underlying the positioning block 35.

With combined reference to FIGS. 4-6B, in addition to the deflection control pull wire 44, endoscope 10' is equipped with a lateral displacement mechanism. As seen in FIG. 4, the pin 40 extends a lateral distance L within the recess 36 across the distal end of endoscope 10'. As noted above, the pin 40 extends through the pin aperture 42 within the positioning block 35. In addition to the deflection capability through rotation about pin 40, positioning block 35 is also configured for lateral displacement relative to the pin 40 along the distance L between left and right sides of recess 36 within the distal end of endoscope 10'.

Positioning block 35 includes surfaces 46a and 46b along opposite lateral sides of the block 35. Lateral displacement pull wires 48a and 48b are each connected at a point along the lateral side surfaces 46a and 46b of the positioning block 35. Pull wires 48a and 48b extend laterally away from the positioning block 35 where they wrap around and extend proximally away from force transmission posts 50, which extend upwardly within the endoscope recess 36. As seen in FIGS. 5-6B, proximal actuation of pull wire 48a results in rightward lateral displacement of the positioning block 35 along the guide of pin 40. Conversely, proximal actuation of pull wire 48b results in leftward lateral displacement of the positioning block 35 along the guide of pin 40. The placement of left and right force transmission posts 50 permit the transfer of a proximally directed force along either of pull wire 48a and 48b into a laterally transmitted force for displacement of the positioning block along the lateral distance L. Pull wires 48a and 48b therefore will exhibit some degree of flexibility in order to bend about posts 50 and allow for slack during rotation of positioning block 35.

The point of connection for lateral pull wires 48a and 48b should be selected in order to result in the least amount of interference with the rotation deflection of the positioning block 35 about rotation pin 40 through actuation of the deflection control wire 44. For example, as seen in FIGS. 4-6A, connection of lateral pull wires 48a, 48b and positioning block 35 may occur at a point just proximal of the aperture 42. The illustrated connection point is intended to be non-limiting and alternative connection locations are permitted with a focus on reducing any interference with the free actuation of deflection wire 44. In addition, the pull wire arrangement illustrated for lateral displacement is also intended to be non-limiting and alternative mechanisms for achieving lateral displacement of positioning block 35 are possible. Any alternative mechanical force transfer mechanism which transfers a back and forth force into a laterally directed force, such as, for example, a rack and pinion gear mechanism, can be utilized.

For example, FIG. 6B depicts a top view of an alternative positioning block 35'. As seen in FIG. 6B, the arrangement for the positioning block 35' only requires a single pull wire 49 instead of the two lateral pull wires 48a and 48b required by the arrangement of FIG. 6A. The single pull wire 49 connects to one side of the positioning block 35' and a spring 51 connects to another side of positioning block 35', opposite the surface of connection for pull wire 49. The end of spring 51 that is not attached to the positioning block 35' can be secured to an internal surface of the underlying endoscope within the recess 36. In addition, the arrangement of FIG. 6B, differs from that of FIG. 6A, in that it includes only a single force transmission post 50 for interaction with pull wire 49. During a procedure, the positioning block 35' can then be manipulated and laterally displaced upon proximal actuation of the pull wire 49. Upon removal of an actuation force on positioning block 35' through the pull wire 49, the spring 51 acts on the positioning block 35' to return it to an initial resting position.

FIGS. 7A-7C illustrate perspective, front, and side views, respectively, of a distal part of an endoscope 10" utilizing a combined lateral displacement and deflection controlled positioning block, according to an embodiment of the present invention. FIG. 7A, for example, illustrates a perspective view of a distal portion of the endoscope 10" including the operation window 32 including positioning block 35 for manipulation of a treatment instrument as well as a visualization device 52 and a lighting device 54 for viewing an internal body portion. Referring to the front view of FIG. 7B, lateral displacement of positioning block 35 between left and right ends of the length L is illustrated. As explained above, actuation of lateral pull wires 48a and 48b allow more precise manipulation of an extended treatment instrument 20 without trauma-causing movement of the underlying endoscope 10". In particular, the combined lateral movement and rotation of positioning block 35 allows for precise manipulation of a treatment instrument through two degrees of freedom as opposed to the single positioning degree of freedom afforded by past elevator rotation systems.

FIG. 7C depicts a side view of the distal portion of endoscope 10" and in particular, the deflection of a treatment instrument 20 as it extends from a working channel of the endoscope 10". Actuation of deflection pull wire 44 causes rotation of positioning block 35 in order to increase or decrease the deflection angle β (as shown in FIG. 7C) at which the treatment instrument extends from the working channel of underlying endoscope 10". For example, rotation of positioning block 35 about pin 40 can cause deflection of treatment instrument 20 between an angle of about 30 degrees to about 135 degrees relative to the longitudinal axis of the endoscope 10".

Figures 8A, 8B, 8C, 8D:
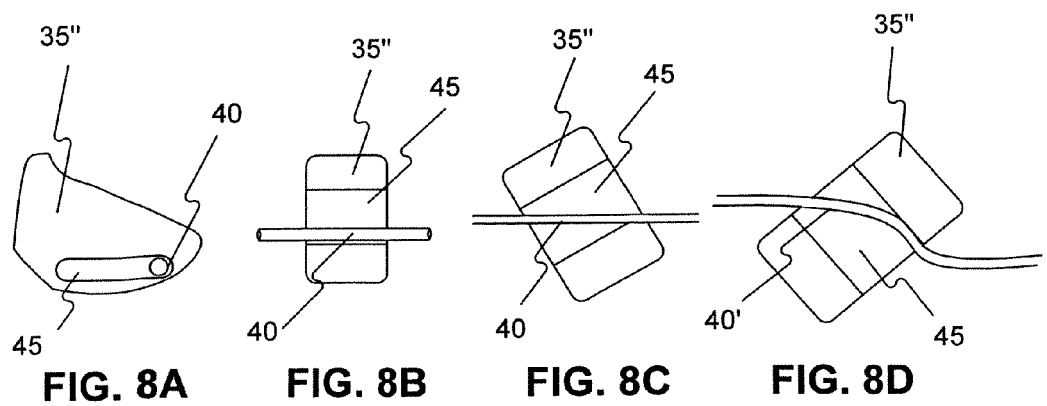
FIG. 8A is a side view of components of an alternative instrument positioning device according to an embodiment of the present invention.
FIGS. 8B-8D are top views of components of alternative instrument positioning devices according to embodiments of the present invention.

FIG. 8A is a side view of components of an alternative instrument positioning device according to an embodiment of the present invention. FIG. 8A depicts an alternative positioning block 35" similar to the positioning block 35 as previously described, with the feature of an elongated pin slot (or channel) 45 replacing the pin aperture 42 described above. The inclusion of the elongated pin slot 45 allows for a predetermined amount of controlled longitudinal (both in a distal and a proximal direction) displacement of the positioning block 35" relative to the underlying endoscope.

The length of elongated pin slot 45 dictates the extent of longitudinal displacement for positioning block 35". At the distal-most and proximal-most displacement positions for positioning block 35", further movement of the positioning block 35" is prevented due to the engagement between an internal surface of the pin slot 45 and the rotation pin 40, housed therein. Back and forth movement of the positioning block 35" within a recess 36 of an underlying endoscope can be caused by any force actuation mechanism capable of displacing the positioning block 35". Examples include, but are not limited to, pull wires, pushable stylets, fluid pressure actuated force transmission mechanisms, and expandable balloons. The slot 45 may be filled with a compliant, self-healing material, such as a sponge material, for example. The inclusion of a sponge material within the slot 45 allows for stabilization of the pin 40 therein such that the pin returns to a centered rest position once a displacement force is no longer transmitted to the positioning block 35".

Rotation of the positioning block 35" relative to the pin 40 (in order to achieve deflection of a treatment instrument as illustrated in FIG. 4, for example) can be achieved by maintaining the longitudinal position of the positioning block 35" within the recess 36 and then causing controlled rotation of the positioning block 35" in the manner described above. Maintaining the longitudinal position of the positioning block 35" can be achieved through any type of known active of passive position locking mechanism.

FIGS. 8B and 8C illustrate partial cross-sectional views of the positioning block 35" depicting the position of pin 40 within the slot 45. As seen in FIGS. 8B and 8C, the area of the slot 45 allows for the capability of partial angular displacement of the positioning block 35" within the housing recess. Accordingly, in addition to the pure lateral and longitudinal displacement capability for the displacement block 35", the area of slot 45 allows for partial angular displacement (as seen in FIG. 8C) that allows for greater range of movement for the positioning block 35".

FIG. 8D illustrates a partial cross-sectional view of the positioning block 35" depicting an alternative flexible rotation pin 40' disposed within the slot 45. The use of the flexible rotation pin 40' allows for further controlled angular displacement of the positioning block 35". As seen in FIG. 8D, the flexible characteristics of pin 40' allow for further angular displacement of the positioning block 35" beyond what is capable in an arrangement where the rotation pin is rigid. Control of the angular displacement of the positioning block 35" can be effectuated though the use of any known force transmission mechanism.

Figure 9:
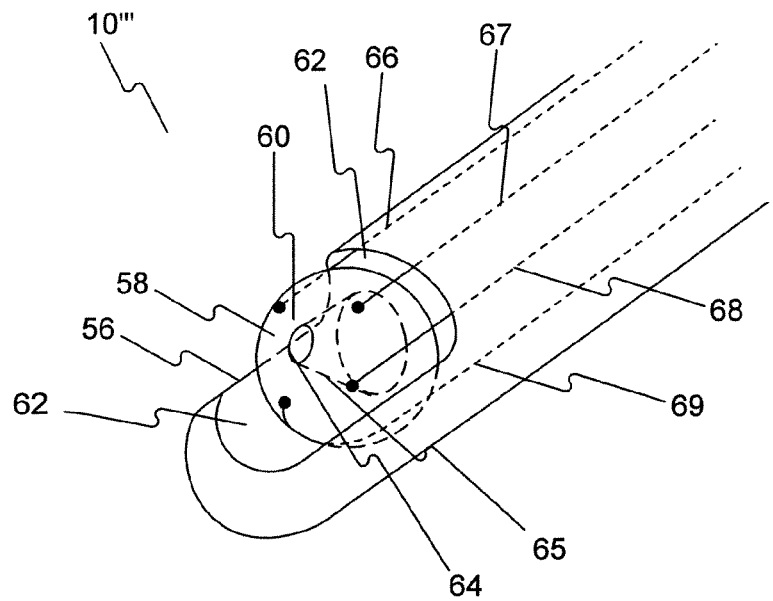
FIG. 9 is a perspective view of a distal part of an endoscope according to another embodiment of the present invention.
Figure 10:
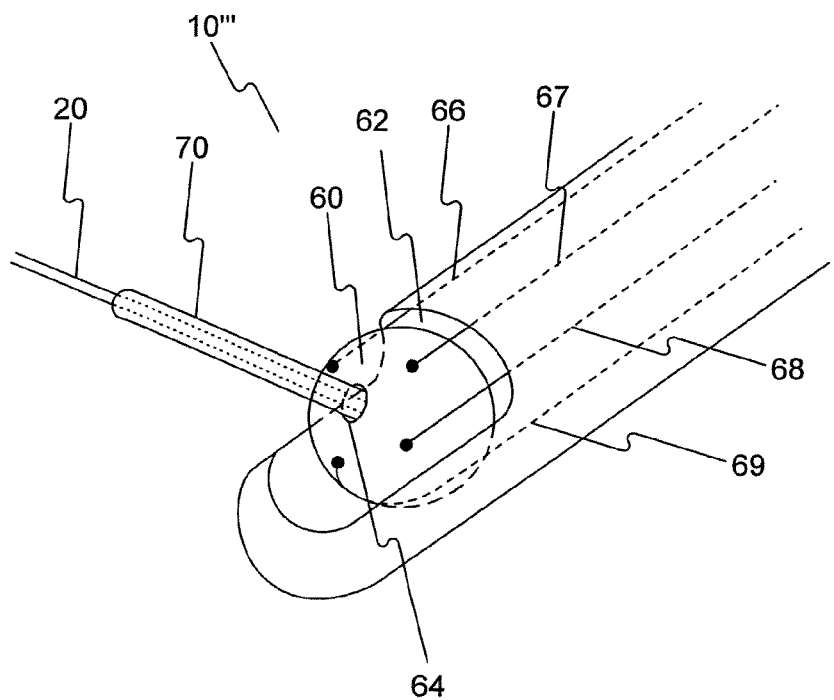
FIG. 10 is a perspective view of a distal part of an endoscope and a treatment instrument according to another embodiment of the present invention.

FIG. 9 is a perspective view of a distal part of an endoscope according to another embodiment of the present invention. FIG. 9 depicts a distal portion of an endoscope 10''' including an operation window 56 in part forming an aperture 62 that houses a roller 60. For example, the size of roller 60 can be selected to be retained within an operating window aperture 62. Roller 60 includes a lumen 64 therethrough that forms an extension of a working channel (not shown) of endoscope 10''', such that a treatment instrument can be extended through the distal opening of lumen 64 during a medical procedure. The roller 60 can be provided in any shape so long as it is rotatably housed within the aperture 62. Roller 60 may be housed within aperture 62 such that a ball and socket type connection joint is formed. For example, roller 60 can be formed of a spherical shape as illustrated in FIGS. 9 and 10. Alternatively, roller 60 can be formed to exhibit a cylindrical shape, an oblong, curved football shape, for example, or any three dimensional structure exhibiting a partially curved exterior surface configured for moving the opening of lumen 64 relative to the endoscope 10''' while housed within aperture 62. Accordingly, the relative shapes of roller 60 and aperture 62 should be coordinated in order to facilitate the housing and movement of roller 60 therein.

As noted above, roller 60 is configured for rotation within aperture 62 such that the opening of lumen 64 can be directed for more precise manipulation of a treatment instrument extending therethrough. Lumen 64 extending through the roller 60 is configured for receiving a treatment instrument as the treatment instrument extends distally through an interior working channel of endoscope 10'''. Since lumen 64 is configured to movably direct and adjust the direction at which the treatment instrument extends out of the endoscope 10''', the proximal end of lumen 64 must maintain communication with the distal opening of an interior working channel of endoscope 10''' that houses the treatment instrument. In one arrangement, for example, lumen 64 exhibits a cone shape 65, illustrated in FIG. 9. Accordingly, lumen 64 extends distally from a large diameter opening at the proximal end to a relatively narrow diameter at the distal point of exit of lumen 64. Since the proximal end of lumen 64 exhibits a greater diameter opening, alignment and communication is maintained between an interior working channel of endoscope 10''' and lumen 64 as roller 60 is moved relative to the aperture 62.

Roller 60 can be manipulated relative to the housing aperture 62 through a system of pull wires. FIG. 9, for example, illustrates a system of four pull wires 66-69 for manipulation of roller 60. Pull wires 66-69 can be fixedly attached to the roller 60, each at a predetermined distance from the distal exit point of lumen 64. Pull wires 66-69 can each be spaced relative to the distal exit point of lumen 64, such that selective manipulation of each of the pull wires 66-69 allows for a predetermined degree of rotation of roller 60 about at least two orthogonal axes. For example, proximal actuation of wire 68 coupled with a release of tension in wire 66 permits a controlled rotation of roller 60 relative to an axis extending upward in FIG. 9. Tension within some of wires 66-69 may need to be selectively loosened in cooperation with selective tightening of others in the unit in order to permit controlled rotation of roller 60. In one embodiment, the point of connection of each pull wire to roller 60 occurs at a constant predetermined distance from the distal point of exit of lumen 64 through roller 60.

Pull wires 66-69 can be connected for operator manipulation through any type of known wire actuation device at the endoscope handle at the proximal end of the system. As is apparent from FIG. 9, selective manipulation of each of the pull wires 66-69 allows for a predetermined degree of rotation of sphere 60 about three axes, like an eyeball. For example, with reference to FIGS. 3 and 9, controlled manipulation of pull wires 66-69 allows for three degrees of freedom. While a system of four pull wires is disclosed as the manipulation mechanism for roller 60, any alternative mechanism for controlled displacement of the roller can be used. For example, alternative mechanisms for rotation of roller 60 (some of which are more particularly described below, with reference to FIGS. 11-13) include specifically positioned and controllable track rollers, an arrangement of three pull wires, or controlled actuation of selectively placed piezoelectric transducers.

FIG. 10 depicts an arrangement of a distal portion of an endoscope similar to that of FIG. 9 and further including an additional positioning mechanism for manipulation of a treatment instrument 20. In FIG. 10, a treatment instrument 20 is extended through an opening of a lumen 64 that extends through roller 60. Within lumen 64 of FIG. 10, extends a slidable sleeve 70 configured for movement relative to the lumen 64 within which it is housed. Sleeve 70 can be configured to exhibit a predetermined level of rigidity such that a treatment instrument 20 extended therethrough will be reliably directed coincident with the direction sleeve 70 extends from lumen 64. For example, during a treatment procedure, sleeve 70 can be used to position the point in space at which the distal end of a treatment instrument 20 is located within a patient's body. This further positioning adjustment mechanism is advantageous in that the distal end of a treatment instrument can be precisely located without requiring repeated manipulation and trauma-casing movement of the entire underlying endoscope body. If the extended sleeve 70 is easily deflected and collapsible during contact with internal body tissues, proper control and repeatable placement of sleeve 70 (and in turn, the treatment instrument 20 extended therethrough) may not be possible. Accordingly, construction of sleeve 70 with a predetermined level of rigidity is advantageous.

Forward and backward movement of sleeve 70 within lumen 64 and the internal working channel of endoscope 10''', in combination with controlled rotation of roller 60, allows for more precise positioning of treatment instrument 20 during a medical procedure. Sleeve 70 may be configured for back and forth movement within lumen 64 through a pushable actuation wire (not shown) proximally extending through endoscope 10'''. For example, the actuation wire could be configured for connection to the proximal end of sleeve 70 such that back and forth movement of the actuation wire through endoscope 10''' is translated into back and forth movement of sleeve 70.

The addition of slidable sleeve 70 within lumen 64 also affords an added two degrees of freedom to the endoscope system. As noted above, sleeve 70 can be manipulated by an operator to move forward and backward within lumen 64. In addition, sleeve 70 can be sized to receive and engage the exterior surface of the treatment instrument 20 through a friction fit, such that controlled rotation of sleeve 70 within lumen 64 effectuates rotation of a treatment instrument 20 extending therein. In addition, sleeve 70 can be configured to engage the treatment instrument 20 in a friction fit such that back and forth movement of sleeve 70 effectuates back and forth displacement of instrument 20. Alternatively, the controlled rotation of treatment instrument 20 by rotation of sleeve 70 can be effectuated through a complimentary groove and recess arrangement between the interior surface of sleeve 70 and the exterior surface of the treatment instrument 20. Accordingly, a treatment instrument 20 can be precisely manipulated through controlled rotation of roller 60, through forward and backward movement of sleeve 70, and through rotation of sleeve 70, to impart rotation to treatment instrument 20.

Figure 11:
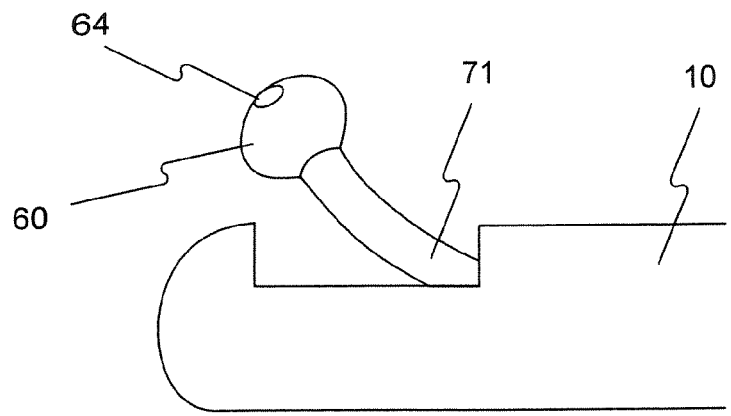
FIG. 11 is a side view of a distal part of an endoscope according to another embodiment of the present invention.

FIG. 11 depicts a side view of a distal part of an endoscope according to another embodiment of the present invention. In FIG. 11, a generic endoscope 10 is depicted housing a positioning sleeve 71 therein. The positioning sleeve 71 includes a roller 60 positioned at the distal end thereof. The positioning sleeve 71 can itself be manipulated and positioned relative to the underlying endoscope 10. In addition, the roller 60 at the distal end of the positioning sleeve 71 can also be precisely rotated and positioned relative to the sleeve 71. Just as in the embodiments of FIGS. 9-10, the roller 60 includes a lumen 64 for receiving a treatment instrument therein. The angular position of a treatment instrument can then be precisely controlled through controlled rotation and positioning of the roller 60 relative to the sleeve 71. Such controlled rotation can be effectuated through a system of pull wires, as described above, or through any other force transmission mechanism capable of moving roller 60.

Figure 12:
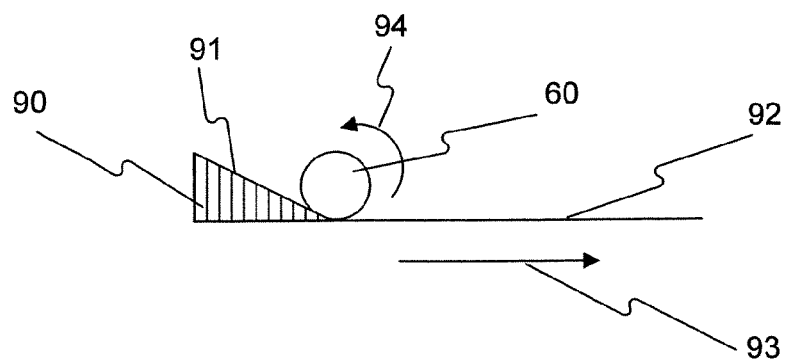
FIG. 12 is a side view of components of an alternative instrument positioning mechanism according to an embodiment of the present invention.

FIG. 12 depicts a side view of components of an alternative instrument positioning mechanism for the roller 60 described in FIGS. 9-11. As seen in FIG. 12, rotation of roller 60 can be effectuated through proximal movement of a wedge 90 connected to a pull wire 92. The wedge 90 includes an inclined surface 91. Interaction between the inclined surface 91 of the wedge 90 and the exterior surface of the roller 60 leads in turn to controlled rotation of the roller 60 upon proximal actuation of the pull wire 92. For example, due to the interaction of the roller 60 with the inclined surface 91, proximal movement of the wedge 90 and the pull wire 92 in the direction of arrow 93 results in rotation of roller 60 in the direction of arrow 94. The particular materials for the exterior surface of roller 60 and the inclined surface 91 can be selected to decrease the amount of sliding therebetween.

Figure 13:
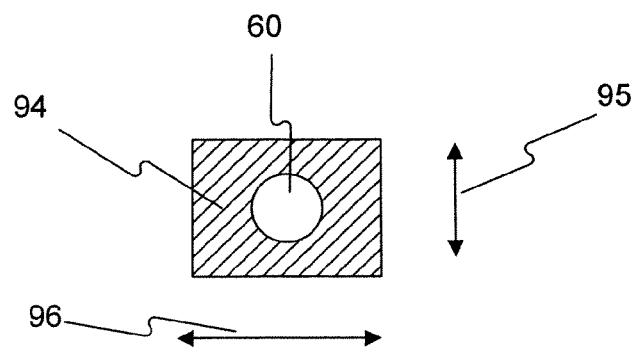
FIG. 13 is a top view of components of an alternative instrument positioning mechanism according to an embodiment of the present invention.

FIG. 13 depicts a top view of components of an alternative instrument positioning mechanism for the roller 60 described in FIGS. 9-11. Instead of the moveable wedge 90 described in FIG. 12, FIG. 13 depicts a movable base component 94, upon which roller 60 rests. Due to the interaction between roller 60 and the surface of base component 94, controlled lateral and longitudinal displacement of the base component 94 within an endoscope recess 36 results in controlled rotation of roller 60. Movement of the base component 94 can be effectuated in both longitudinal directions designated by arrow 95 as well as lateral directions designated by arrow 96.

In all of the embodiments described above, the particular positioning mechanism for a treatment instrument can be equipped with any type of known locking mechanism for the purpose of releasably maintaining a particular position of a treatment instrument relative to an endoscope.

Figure 14:
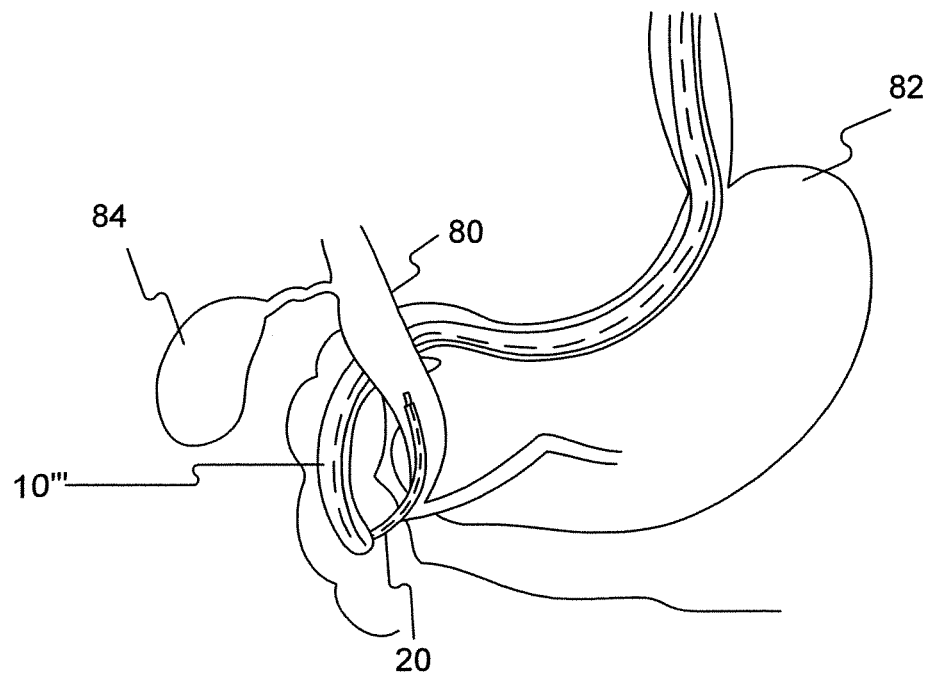
FIG. 14 illustrates the positioning of an endoscope and treatment device within a patient's body portion.

FIG. 14 illustrates the positioning of an endoscope 10', 10", or 10''' and treatment device 20 within a patient's body portion. In particular, FIG. 14 depicts the extension of a treatment instrument 20 within a particular bile duct 80 during an ERCP procedure. As seen in FIG. 14, the endoscope 10''', for example, is inserted and extended through a patient's stomach 82 such that the distal end and aperture 62 (not shown) of endoscope 10''' are positioned is close relation to a particular bile duct 80 leading to, for example, gall bladder 84. As seen in FIG. 14, treatment instrument 20 is extended beyond the internal working channel of endoscope 10'''. The treatment instrument can then be precisely manipulated, for example, by controlled rotation of roller 60 and/or the additional extension of sleeve 70 beyond endoscope 10''', described above. In addition, further manipulation of instrument 20 can be effectuated through rotation of sleeve 70, for example.

Precise manipulation of treatment instrument 20 allows for more precise positioning and location of instrument 20 such as, for example, during placement of instrument 20 within a particular bile duct 80 of interest. More precise manipulation of a treatment device 20 can result in shortened treatment procedures by reducing the amount of time necessary to effectuate proper position of the treatment device 20. In addition, controlled deflection of the angle at which treatment device 20 exits the underlying endoscope 10''' can reduce internal tissue trauma caused during endoscopic procedures requiring repeated repositioning and manipulation of the entire endoscope during location of the endoscope. For example, the positioning mechanisms described above facilitate the location of treatment instrument 20 within a particular bile duct 80 such that the duration of, and occurrence of tissue trauma during, a treatment procedure can be reduced.

While the above described positioning system has been depicted as utilizing pull wire manipulation mechanisms, the invention it not intended to be limited to this particular structure. Therefore, alternative actuation devices are intended to be within the scope of this invention, including all equivalent structures known for transferring endoscopic manipulation forces along the longitudinal axis of an endoscope. Furthermore, unless expressly stated as otherwise, all components and elements of one of the various disclosed embodiments can be used, either via substitution, or in addition with the components and elements of any of the other embodiments.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   an elongated flexible tube including a distal end and a proximal end, and defining a lumen extending from the proximal end to an aperture at the distal end, wherein the aperture is a side-facing aperture opening laterally along the flexible tube;
   a positioning mechanism positioned at the distal end of the flexible tube proximate the side-facing aperture, the positioning mechanism configured for movement through at least two degrees of freedom to transmit force to a treatment instrument extending through the lumen and to control a direction at which the treatment instrument extends from the side-facing aperture, wherein the positioning mechanism includes a sleeve having a roller positioned on a distal end of the sleeve and being rotatable relative to the sleeve, wherein the sleeve and the roller are configured to move relative to the side-facing aperture to extend external the side-facing aperture, wherein the roller is rotatable relative to the side-facing aperture, the roller including a lumen therethrough configured for receiving the treatment instrument extended distally beyond the lumen;

an instrument sleeve extending within the lumen of the roller and movable within and distally beyond the lumen of the roller, wherein the instrument sleeve is configured for receiving the treatment instrument and imparting rotation to the treatment instrument upon rotation of the instrument sleeve; and an actuation wire coupled to a proximal end of the instrument sleeve, wherein longitudinal movement of the actuation member causes longitudinal movement of the instrument sleeve and the treatment instrument.

2. The medical device of claim 1, wherein the positioning mechanism is configured for movement through at least three degrees of freedom.

3. The medical device of claim 2, wherein the positioning mechanism is rotatable about three orthogonal axes.

4. The medical device of claim 1, wherein a proximal end of the lumen through the roller is configured to maintain communication with the lumen of the elongated flexible tube when the roller rotates relative to the aperture.

5. The medical device of claim 1, wherein the lumen through the roller has a distal opening more narrow than a proximal opening.

6. The medical device of claim 1, wherein the roller is configured for rotation about three orthogonal axes.

7. The medical device of claim 6, wherein rotation of the roller relative to the side-facing aperture and the sleeve is achieved through the actuation of pull wires fixedly attached to the roller.

8. The medical device of claim 6, further comprising a wedge having an inclined surface positioned distally of the roller and wherein the rotation of the roller relative to the side-facing aperture is achieved through proximal movement of the inclined wedge surface beneath the roller.

9. The medical device of claim 6, further comprising a movable base positioned distally of the roller and wherein the rotation of the roller relative to the side-facing aperture is achieved through longitudinal and lateral movement of the base beneath the roller.

10. The medical device of claim 7, wherein attachment of each pull wire to the roller occurs at a substantially equal distance from a distal point of exit of the lumen of the roller.

11. The medical device of claim 7, wherein at least three pull wires are fixedly attached to the roller.

12. The medical device of claim 1, wherein the medical device is an endoscope that includes visualization components therein.

13. The medical device of claim 1, wherein the medical device is an endoscope that includes illumination components therein.

14. The medical device of claim 1, wherein the medical device is an endoscope that includes an additional positioning mechanism for achieving controlled deflection of the elongated flexible tube.

15. A medical device, comprising:
an elongated flexible tube including a distal end and a proximal end, and defining a lumen extending from the proximal end to an aperture at the distal end, wherein the aperture is a side-facing aperture opening laterally along the flexible tube;

a roller positioned at a distal end of a sleeve and rotatable relative to the sleeve, the roller including a lumen therethrough configured for receiving a treatment instrument extended distally beyond the lumen, wherein the sleeve and the roller are configured to move relative to the side-facing aperture to extend external the side-facing aperture;

an instrument sleeve extending within the lumen of the roller and movable within and distally beyond the lumen in the roller, wherein the instrument sleeve is configured for receiving the treatment instrument and imparting rotation to the treatment instrument upon rotation of the instrument sleeve; and an actuation wire coupled to a proximal end of the instrument sleeve, wherein longitudinal movement of the actuation member causes longitudinal movement of the instrument sleeve.

16. The medical device of claim 15, wherein the roller is configured for rotation about three orthogonal axes.

17. The medical device of claim 15, wherein the roller is configured to rotate relative to the side-facing aperture, wherein rotation of the roller relative to the side-facing aperture and the sleeve is achieved through the actuation of pull wires fixedly attached to the roller.

18. The medical device of claim 15, further comprising a wedge having an inclined surface positioned distally of the roller and wherein the roller is configured to rotate relative to the side-facing aperture through proximal movement of the inclined wedge surface beneath the roller.

19. The medical device of claim 15, further comprising a movable base positioned distally of the roller and wherein the roller is configured to rotate relative to the side-facing aperture through longitudinal and lateral movement of the base beneath the roller.

20. The medical device of claim 17, wherein attachment of each pull wire to the roller occurs at a substantially equal distance from a distal point of exit of the lumen of the roller.

21. The medical device of claim 17, wherein at least three pull wires are fixedly attached to the roller.

22. The medical device of claim 15, wherein the medical device is an endoscope that includes visualization components therein.

23. The medical device of claim 15, wherein the medical device is an endoscope that includes illumination components therein.

24. The medical device of claim 15, wherein the medical device is an endoscope that includes an additional positioning mechanism for achieving controlled deflection of the elongated flexible tube.

25. The medical device of claim 15, wherein the roller has a spherical shape.

26. The medical device of claim 17, wherein a proximal end of the lumen through the roller is configured to maintain communication with the lumen of the elongated flexible tube when the roller rotates relative to the side-facing aperture.

27. The medical device of claim 15, wherein the lumen through the roller has a distal opening more narrow than a proximal opening.

28. The medical device of claim 15, wherein the longitudinal movement of the actuation member also causes longitudinal movement of the treatment instrument.

29. A medical device, comprising:
an elongate member including a distal end and a proximal end, and defining a lumen extending from the proximal end to a side-facing aperture that opens laterally along the elongate member;

a roller positioned at a distal end of a sleeve and rotatable relative to the sleeve, the roller including a lumen therethrough configured for receiving a treatment instrument extended distally beyond the lumen, wherein the sleeve and the roller are configured to move relative to the side-facing aperture;

an instrument sleeve extending within the lumen of the roller and movable within and distally beyond the lumen of the roller, wherein the instrument sleeve is configured for receiving the treatment instrument and imparting rotation to the treatment instrument upon rotation of the instrument sleeve; and an actuation wire coupled to a proximal end of the instrument sleeve, wherein longitudinal movement of the actuation wire causes longitudinal movement of the instrument sleeve and the treatment instrument.

30. The medical device of claim 29, wherein the roller is configured for rotation about three orthogonal axes.

31. The medical device of claim 29, wherein the roller is configured to rotate relative to the side-facing aperture, wherein rotation of the roller relative to the side-facing aperture and the sleeve is achieved through the actuation of pull wires fixedly attached to the roller.

* * * * *